(12) United States Patent
Barth et al.

(10) Patent No.: US 10,123,808 B2
(45) Date of Patent: Nov. 13, 2018

(54) SURGICAL, TORQUE TRANSFERRING INSTRUMENT INCLUDING ASSOCIATED TOOL

(71) Applicant: Aesculap AG, Tuttlingen (DE)

(72) Inventors: Jürgen Barth, Denkingen (DE); Florian Kraft, Neuhausen ob Eck (DE)

(73) Assignee: Aesculap AG, Tuttlingen (DE)

( * ) Notice: Subject to any disclaimer, the term of this patent is extended or adjusted under 35 U.S.C. 154(b) by 705 days.

(21) Appl. No.: 14/422,301

(22) PCT Filed: Aug. 26, 2013

(86) PCT No.: PCT/EP2013/067643
§ 371 (c)(1),
(2) Date: Feb. 18, 2015

(87) PCT Pub. No.: WO2014/037240
PCT Pub. Date: Mar. 13, 2014

(65) Prior Publication Data
US 2015/0201949 A1  Jul. 23, 2015

(30) Foreign Application Priority Data

Sep. 5, 2012  (DE) ........................ 10 2012 108 265

(51) Int. Cl.
*A61B 17/00* (2006.01)
*A61B 17/16* (2006.01)
(Continued)

(52) U.S. Cl.
CPC ........ *A61B 17/162* (2013.01); *A61B 17/1624* (2013.01); *A61B 17/32002* (2013.01);
(Continued)

(58) Field of Classification Search
CPC combination set(s) only.
See application file for complete search history.

(56) References Cited

U.S. PATENT DOCUMENTS 4,107,949 A    8/1978  Wanner et al.
4,976,655 A   11/1990  Hebert, Sr.
(Continued)

FOREIGN PATENT DOCUMENTS

CH        686113 A5     1/1996
CN        2460053      11/2001
(Continued)

OTHER PUBLICATIONS

Chinese Office Action and Search Report with English language translation for Application No. 201380046430.0, dated Oct. 31, 2016, 13 pages.

(Continued)

*Primary Examiner* — Sameh Boles
(74) *Attorney, Agent, or Firm* — RatnerPrestia

(57) ABSTRACT

A surgical torque-transferring instrument includes a preferably universal handpiece to which a handpiece shaft having an internal torsion rod or an internal tool shaft can be connected. The torsion rod can be connected to a torque transmission train or drive within the handpiece via a plug-type coupling which includes a male and female coupling piece which can be axially plugged into each other. The cross-sectional shape of the two coupling pieces approximately corresponds to a four-leaved cloverleaf.

6 Claims, 15 Drawing Sheets

Figure 1:
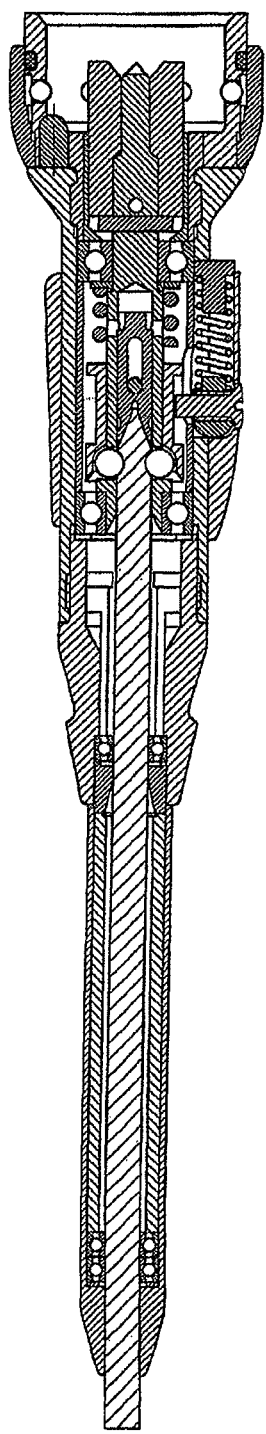

(51) Int. Cl.
*A61B 17/32* (2006.01)
*F16D 1/10* (2006.01)
*A61C 1/14* (2006.01)
*F16D 3/06* (2006.01)

(52) U.S. Cl.
CPC ............... *A61C 1/147* (2013.01); *F16D 1/10* (2013.01); *F16D 3/06* (2013.01); *A61B 2017/00477* (2013.01); *A61B 2017/00486* (2013.01); *A61B 2017/1602* (2013.01); *F16D 2001/102* (2013.01)

(56) References Cited

U.S. PATENT DOCUMENTS

| | | | |
|---|---|---|---|
| 5,634,933 | A | 6/1997 | McCombs et al. |
| 5,735,535 | A | 4/1998 | McCombs et al. |
| 5,871,493 | A | 2/1999 | Sjostrom et al. |
| 5,888,200 | A | 3/1999 | Walen |
| 5,934,846 | A | 8/1999 | Ishii |
| 7,854,659 | B2 * | 12/2010 | Rom ............... F16D 3/18 464/106 |
| 2002/0058958 | A1 | 6/2002 | Walen |
| 2003/0023256 | A1 | 1/2003 | Estes et al. |
| 2003/0199856 | A1 | 10/2003 | Hill et al. |
| 2004/0172035 | A1 | 9/2004 | Parmigiani |
| 2006/0053974 | A1 | 3/2006 | Blust et al. |
| 2006/0263744 | A1 | 11/2006 | Nakanishi |
| 2006/0278049 | A1 | 12/2006 | Baynham |
| 2010/0063524 | A1 | 3/2010 | McCombs |
| 2010/0206099 | A1 | 8/2010 | Diao et al. |
| 2010/0217281 | A1 | 8/2010 | Matsuoka et al. |
| 2011/0098688 | A1 | 4/2011 | Gigon |
| 2011/0196380 | A1 | 8/2011 | Cremer et al. |
| 2015/0088184 | A1 | 3/2015 | McCombs |

FOREIGN PATENT DOCUMENTS

| | | |
|---|---|---|
| CN | 1618579 A | 5/2005 |
| CN | 101810500 A | 8/2010 |
| CN | 102202587 A | 9/2011 |
| DE | 41 03 663 A1 | 8/1992 |
| DE | 2551125 | 5/1997 |
| DE | 29623825 U1 | 2/2000 |
| DE | 19918638 A1 | 11/2000 |
| DE | 103 11 455 B3 | 9/2004 |
| DE | 69726871 T2 | 10/2004 |
| DE | 10 2004 006 930 A1 | 11/2004 |
| DE | 102007036354 A1 | 2/2009 |
| DE | 20 2010 003 324 U1 | 5/2010 |
| DE | 102012101259 | 8/2013 |
| EP | 0056266 A1 | 7/1982 |
| EP | 0430563 A1 | 6/1991 |
| EP | 1356776 A1 | 10/2003 |
| EP | 1 598 023 A2 | 11/2005 |
| EP | 1 820 987 A2 | 8/2007 |
| EP | 2022414 A1 | 2/2009 |
| EP | 2221010 A1 | 8/2010 |
| JP | 4839959 | 6/1973 |
| JP | S58195457 A | 11/1983 |
| JP | 60103715 U | 7/1985 |
| JP | 03163207 A | 7/1991 |
| JP | 07009226 A | 1/1995 |
| JP | 2000015508 A | 1/2000 |
| JP | 2003522584 A | 7/2003 |
| JP | 2006520222 A | 9/2006 |
| JP | 2015527148 A | 9/2015 |
| RU | 2251391 C2 | 5/2005 |
| RU | 59961 U1 | 1/2007 |
| SU | 1598980 A1 | 10/1990 |
| WO | 0160261 A2 | 8/2001 |
| WO | 2010028001 A2 | 3/2010 |

OTHER PUBLICATIONS

German Search Report with partial translation issued in related German Application No. 10 2012 108 265.0, dated Jun. 18, 2013.
Russian Office Action with English language translation for Application No. 2015112110/14, dated Jun. 15, 2017, 12 pages.
International Search Report issued in related International Application No. PCT/EP2013/067643, dated Dec. 2, 2013.
Japanese Office Action with English language translation for Application No. 2015-530347, dated May 15, 2017, 9 pages.
European Communication for European Application No. 13752648.9, dated Oct. 16, 2017 with translation, 11 pages.
Russian Office Action for Russian Application No. 2015112136, dated Oct. 13, 2017, with English language translation, 9 pages.
Japanese Office Action with English language translation for Application No. 2015-530320, dated Mar. 14, 2017, 17 pages.
Chinese Office Action for Chinese Application No. 201380046434.9, dated Oct. 24, 2016, including English translation, 17 pages.
Russian Office Action for Russian Application No. 2015112137, dated Oct. 13, 2017, with English translation, 9 pages.
Japanese Office Action with English language translation for Patent Application No. 2015-530345, dated May 16, 2017, 8 pages.
Russian Office Action with English language translation for Patent Application No. 2015112137/14, dated Jun. 15, 2017, 13 pages.
German Search Report with partial translation issued in related German Application No. 10 2012 108 264.2, dated Jun. 17, 2013, 6 pages.
International Search Report issued in related International Application No. PCT/EP2013/067639, dated Dec. 4, 2013, 3 pages.
Japanese Office Action with English language translation for Application No. 20150530346, dated May 16, 2017, 8 pages.
International Search Report issued in related International Application No. PCT/EP2013/067641, dated Dec. 2, 2013, 3 pages.
International Search Report issued in related International Application No. PCT/EP2013/064612, dated Dec. 2, 2013, 3 pages.
German Search Report with partial translation issued in related German Application No. 10 2012 108 267.7, dated Mar. 12, 2013, 6 pages.
Russian Office Action for Russian Application No. 2015112136, dated May 26, 2017, 11 pages.
German Search Report with partial translation issued in related German Application No. 10 2012 108 266.9, dated Mar. 12, 2013, 6 pages.

* cited by examiner

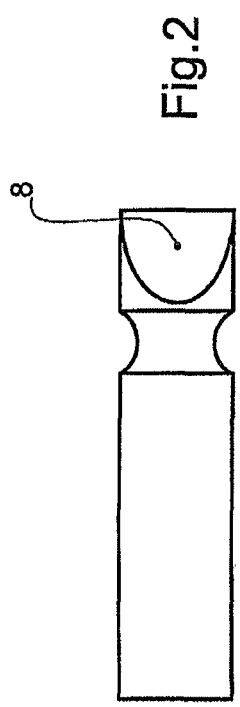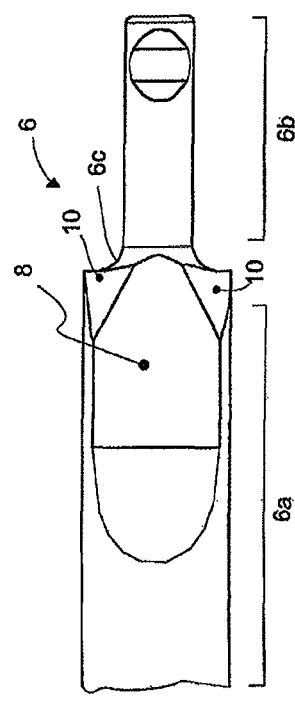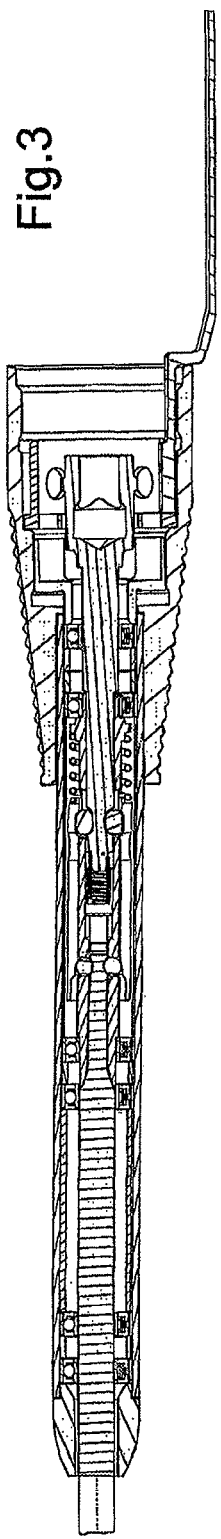

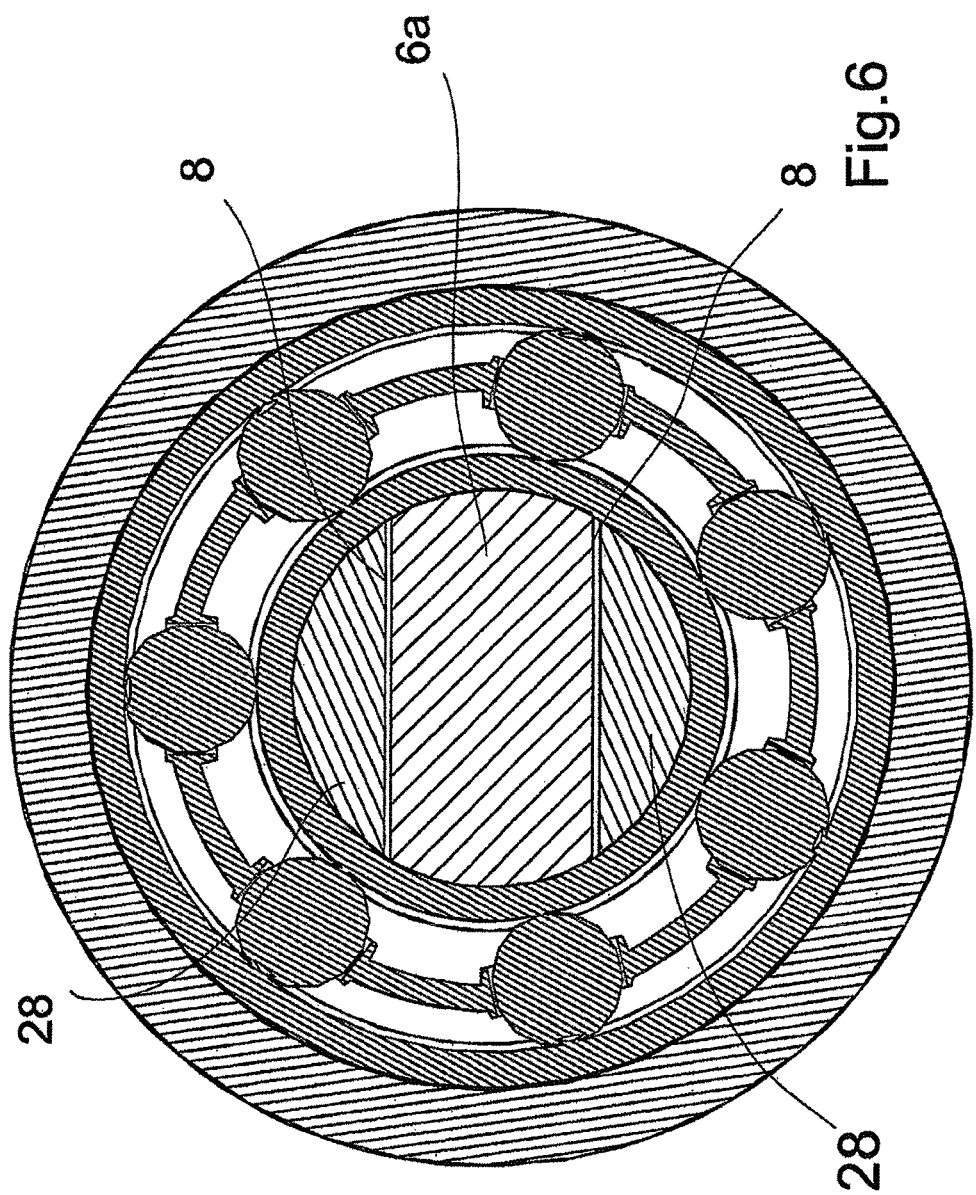

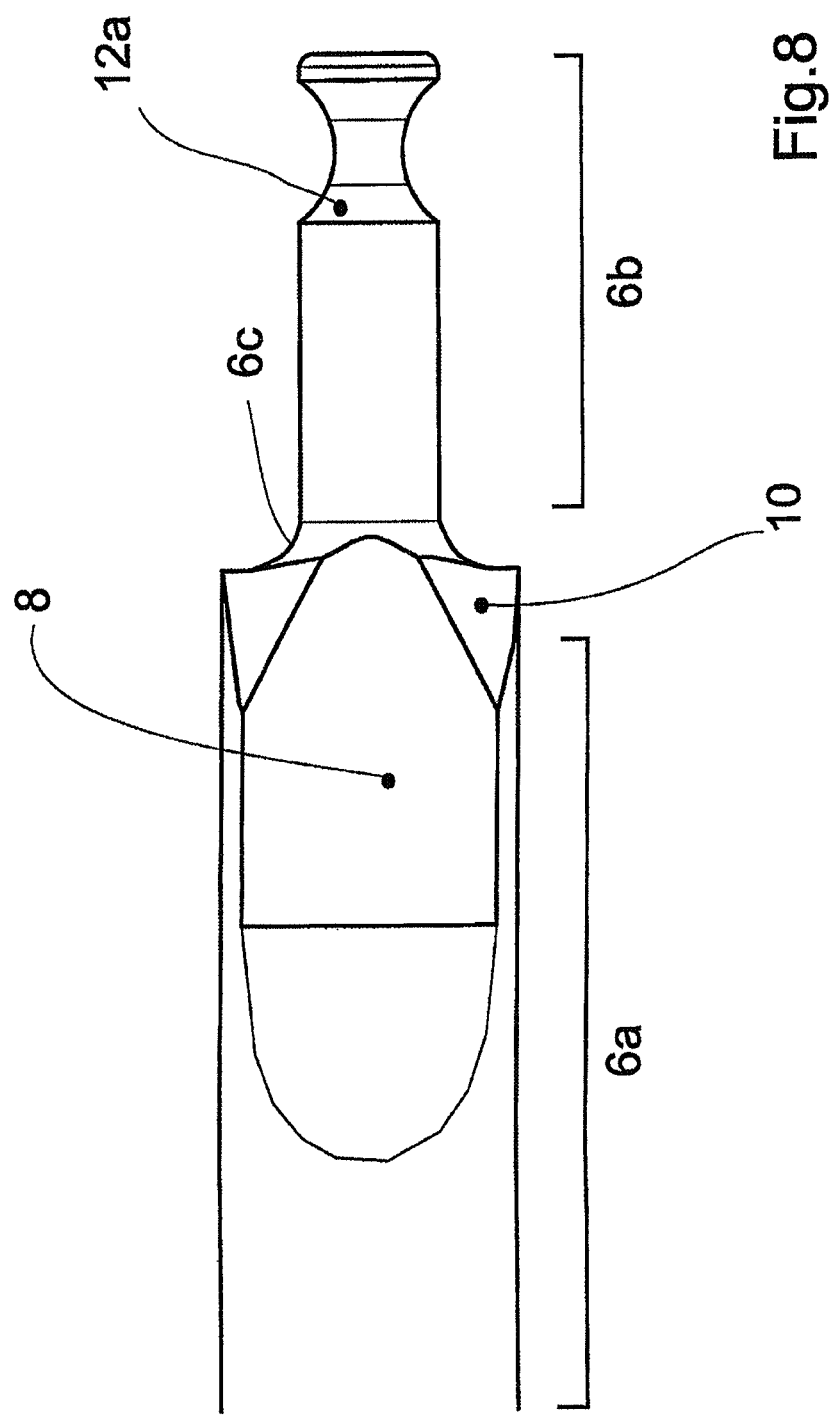

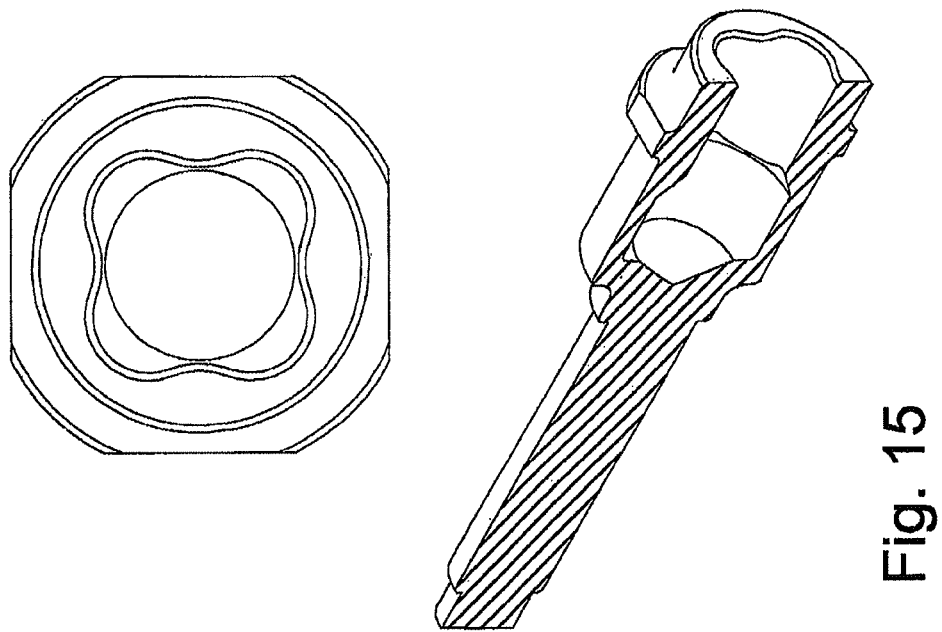
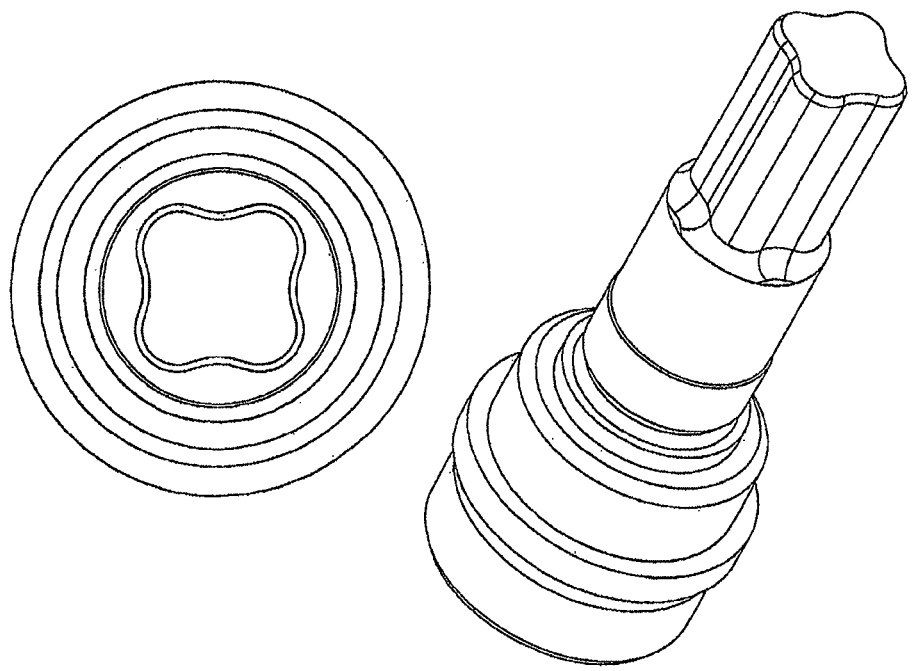
Fig. 15

SURGICAL, TORQUE TRANSFERRING INSTRUMENT INCLUDING ASSOCIATED TOOL

RELATED APPLICATIONS

This application is the U.S. National Phase of International Application No. PCT/EP2013/067643, filed Aug. 26, 2013, which claims the benefit of priority of German Application No. 10 2012 108 265.0, filed Sep. 5, 2012, the contents of both applications being incorporated by reference herein in their entireties.

FIELD

The present invention relates to a surgical instrument for providing a torque as well as a driven tool which is rotatably supported in the instrument handpiece or a handpiece shaft connected thereto and to which a torque can be transmitted which is as high as possible.

BACKGROUND

In the advanced (minimally invasive) surgery, instruments are used for instance for a chip-removing or material-removing machining of bones, cartilages etc., for example with arthroscopic operations, in spinal surgery and similar orthopedic treatments, which comprise an ergonomically shaped handpiece and an optionally exchangeable tool (such as a milling cutter, turning knife, polishing head, etc.) which is rotatably supported in the handpiece at its distal end so as to be able to be driven. Depending on the designated use and the intended rotational speed, the tool drive is a hydraulic, pneumatic or electromotive drive which is in operative connection with the tool via a torque transmission train (such as a gearing mechanism and/or a number of shafts which may possibly be coupled to one another) within the handpiece. The drives may be integrated in the handpiece or implemented as external drive units which are coupled to the handpiece via energy supply lines or torque transmission lines (e.g. flexible and elastic shafts); in this case, the handpiece essentially serves only for accommodating the gearing mechanism or torque transmission train.

Tubular handpiece shafts are usually connected/mounted to the distal ends of the handpieces, i.e. the ends facing the body, and depending on the intended purpose said handpiece shafts have different shaft lengths and shapes to advance to various places within a patient body. By way of example, there are straight or bow-shaped handpiece shafts or preferably those which are cranked (angled) in the zone where they are fitted to the handpiece; in said handpiece shafts, a torque transmission rod or shaft (in the following: torsion rod) is always supported. Said rod/shaft has to be sufficiently stiff (resistant to torsion) in order to be able to transfer the required torque to a tool which is distally inserted therein or formed thereon (i.e. the rod needs to have a sufficiently high torsional stiffness), but also has to be sufficiently flexible, i.e. possess a certain bending flexibility, in order to be capable of following the curvatures of a (not straight) handpiece shaft route also in the presence of a rotary movement.

For connecting the tool to the torsion rod supported in the handpiece shaft, a shaft coupling is provided for detachably receiving a tool shaft. In such arrangement, however, one problem is to provide such a shaft coupling for the possibly exchangeable tool within the small-diameter handpiece shaft with such a design that a safe and long-lasting function of the surgical instrument is ensured even with such small handpiece shaft diameters and high rotational speeds, especially also with long handpiece shafts. Moreover, also the handpiece shaft should be exchangeably received on the handpiece in order to be able to realize different shaft lengths and shapes with a single handpiece. Here, the crucial point is the additional detachable torque-based connection between the gearing mechanism/torque transmission train accommodated in the handpiece and the torsion rod supported in the shaft; on the one hand, said connection is required to be closed in an easy and simple manner and on the other hand it is supposed to transfer sufficiently high torques. Finally, the operability of the instrument (including the process of exchanging a tool and/or a handpiece shaft) should be simple and safe.

A surgical instrument of this kind and in particular a handpiece of such a surgical instrument is known from EP 1 598 023 A2, for example.

In this special case, the known handpiece consists of a sleeve-shaped handle portion (which could have any other handle shape, of course) which has a proximal end (facing away from the body) to which a line package for power supply (pressurized air, electrical current or hydraulic pressure) can be connected and a distal end (facing the body) to which a handpiece shaft is screwed (optionally in exchangeable fashion) by means of a union nut. The handpiece shaft has an outer and an inner shaft jacket which also serves for slidably and rotationally guiding the torsion rod inserted therein. In the axial direction, the inner shaft jacket is subdivided in several segments between which one ball bearing each is inserted in the outer shaft jacket, said ball bearings supporting the torsion rod on the outer shaft jacket. A tool, preferably a milling head is fixed or formed on the distal end of the torsion rod.

As can be taken from this reference, the tool is basically formed from an engagement or cutting head and the torsion rod, which are connected to each other in one piece. Thus, the coupling between the tool and the gearing mechanism/torque transmission train within the handle portion is achieved exclusively in the area of the union nut. This means that the tool is a custom-made article which is especially adapted in its length to said one, specific handpiece shaft and cannot be used for other handpiece shafts having another length. It is obvious that such a design principle is expensive to manufacture as well as in providing it, as a matching tool has to be present or to be stored for each handpiece shaft.

The attached FIG. 1 schematically illustrates the longitudinal section of such a known surgical instrument in which a tool has already been inserted.

According to that, the known tool comprises the tool shaft which projects out of the distal end of the instrument shaft or handpiece shaft so as to be rotatable and has its distal end provided with a cutting head (not shown in further detail). The proximal tool shaft end illustrated in FIG. 2 in an enlarged view is provided with the known tool shaft in the form of a sharpened wedge shape, forming two inclined surfaces (corresponding to a so-called dihedron) facing away from each other and serving for introducing a torque. On the distal end portion of said wedge shape, the tool shaft is formed with a circumferential groove which serves as an axial locking means as will be described below.

In accordance with the above tool construction, the known handpiece has its distal end provided with an axially shiftable cap sleeve by means of which the instrument shaft or handpiece shaft can be coupled to the handpiece in torque-proof fashion. Within the handpiece in the area of the cap sleeve, a rotatably supported accommodation tube is provided which has its proximal end portion put into a rotary spindle and secured in torque-proof fashion therein by means of across pin.

Formed on the distal end of the accommodation tube are at least two diametrically opposing holes which have clamping balls movably inserted therein. A closure or clamping sleeve is supported so as to surround the outside of the accommodation tube and so as to be axially shiftable; in a first axial position, said clamping sleeve unblocks the clamping balls so that they can move radially outwards, and in a second axial position it urges the clamping balls in radially inward direction. For the manual operation of the clamping sleeve, a slider is also provided which is supported on the outside of the handpiece and connected to the clamping sleeve by means of a driving pin. In this context, it is to be noted that the slider is spring-biased toward the second axial position of the clamping sleeve.

As can be further taken from FIG. 1, a torque transmission bolt is provided within the accommodation tube so as to be relatively shiftable in axial direction; said bolt comprises a distally arranged, axially extending wedge-shaped notch which can be made to engage the wedge shape of the tool shaft for torque transmission. The bolt is biased in distal direction by means of a spring and is secured in the accommodation tube by a cross pin in torque-proof manner.

According to said constructional design, the known tool—with its tool shaft ahead—has to be inserted into the handpiece shaft at the distal tip thereof and has to be axially shifted therein toward the accommodation tube until the proximal tool shaft wedge (dihedron) rests against the clamping balls. At that moment, the clamping sleeve is axially shifted to its release position via the slider, so that the clamping balls are displaced by the tool shaft wedge in radially outward direction and in this way is able to further advance into the accommodation tube until it comes to lie in the notch of the torque transmission bolt. If the slider is released again, the clamping sleeve (driven by the pretensioning spring) automatically returns to its clamping position in which the clamping balls are urged radially inwards into the circumferential groove on the tool shaft and hence lock the tool shaft in axial position. In this way, a torque can be transferred from the rotary shaft through the cross pin, the accommodation tube, the further cross pin and the torque transmission bolt (torque transmission train) to the tool shaft.

The known construction described above, however, has some particular features which are in need of improvement:

The described cross pin connections result in a local weakening of the material in the torque transmission bolt as well as in the accommodation tube and also in the rotary shaft within the handpiece. In addition, the cross pins are quite thin and therefore prone to breakage. As a whole, the transferable torque is limited.

Furthermore, the wedge shape of the tool shaft is not very suitable for transferring high torques, as the axially acting force amount results in the tool-side wedge shape becoming disengaged from the notch of the torque transmission bolt. Moreover, it has to be expected that the accommodation tube is spread apart in the area of the notch. With this design, the entire coupling-related mechanic system for connecting the tool shaft to the gearing mechanism/torque transmission train within the instrument handpiece has been displaced to the area of the cap sleeve where there is still a sufficient amount of radial clearance for receiving the coupling elements. As a consequence, the tool shafts have to span the full length of the instrument shafts or handpiece shafts. This means that special tools are required for each handpiece shaft.

If there is the intention to replace the individual system known per se and consisting of the handpiece, the handpiece shaft connectable to it as well as the associated tool by a so-called universal system in which several tools can be inserted in one handpiece shaft, provisions have to be taken which are capable of preventing the use of a tool which would be a wrong one for a specific handpiece shaft. Such provisions, however, are not suggested in the known prior art.

SUMMARY

In the light of said prior art, it is the object of the present invention to provide a tool for a surgical torque-transferring instrument as well as a system (surgical instrument) preferably consisting of an instrument handpiece and at least one (or more) tool (s) according to the invention, which each allow to achieve a better functionality. Preferably, the instrument is supposed to be able to transfer high torques on the whole; more preferably, it should have an easy and safe handling. One of the aims is to reduce the production and provisioning costs for the system/instrument by using universal tools for different (exchangeable) handpiece shafts.

The above object as well as the other advantageous aims of the invention are achieved by a coupling comprising the features described herein, as well as by a surgical instrument comprising the features described herein.

Accordingly, the gist of the present invention is to develop a coupling between the torsion rod supported in an exchangeable handpiece shaft and a torque transmission train (gear unit or drive) received in the universal handpiece.

Specifically, the coupling comprises two coupling pieces, i.e. a male coupling piece preferably on the part of the torque transmission train in the handpiece and a female coupling piece on the proximal end of the torsion rod supported in the handpiece shaft; said coupling pieces have a mutually compatible cross-sectional shape such that the male coupling piece can be inserted into the female coupling piece in the axial direction of the torsion rod so as to be torque-proof, but axially movable. The cross-sectional shape of the two coupling pieces approximately corresponds to a four-leaved cloverleaf. This allows to reduce the notch effect in the circumferential direction and to lower the risk of a self-retention effect. This helps to be able to reliably transfer higher maximum torques to the torsion rod and at the same time to maintain the possibility of axially moving the two coupling pieces relative to each other. This means that the profile which is approximated according to the invention'to the four-leaved cloverleaf shape allows to realize a coupling for transferring a sufficiently high torque from a surgical handpiece to a surgical tool, with one axial degree of freedom remaining.

Moreover, it has turned out that a cross-sectional shape of this type basically improves the radial guidance of the torsion rod so that the coupling area can be implemented without any additional radial bearings for radially supporting the coupling. This results in a sufficient radial installation space for the coupling itself as well as for various connections for fixing the handpiece shaft to the handpiece.

It is preferred that the cross-sectional shape, according to the invention, of the coupling piece is composed of four identical circles which have a smaller radius and define the four corners of the cross-sectional shape of the coupling, said circles being arranged so as to be angularly offset by 90° relative to each other, resulting in an axially symmetric shape. Each two neighboring circles are geometrically connected to each other by a further circle having a larger radius, whose center—other than those of the corner circles—is situated outside the cross-sectional shape. This means that the side circle line which connects respectively two neighboring circles receives an (elongated) concave contour which merges into a (clinched) convex contour in the area of the corner circles, approximating the cloverleaf shape in the end.

More preferably, the side circle line touches the two neighboring corner circles in tangential manner, so that the overall coupling contour created in this way results in a continuous circumferential line (without any edges and corners).

In geometric view, the cross-sectional contour preferably meets the following conditions:

If a value A represents the diameter of a circumscribed circle which has its center in the center of the cross-sectional shape and has radially outer contact points on all corner circles and a value B is the clearance (distance) between two opposing concave side circle lines, the following calculation formulas can be applied for the optimization of the cross-section:

$$B = kB * A \quad (1)$$

with $0.6 < kB < 0.9$.

The radius Re of each corner circle preferably has the following relationship to the value A.

$$Re = kRe * A \quad (2)$$

with $0.6 < kRe < 0.9$.

The radius Ri of each side circle preferably has the following relationship to the value A.

$$Ri = kRi * A \quad (3)$$

with $0.8 < kRi < 1.5$.

The invention will be explained in more detail below by means of a preferred exemplary embodiment as well as several variants with respect to the accompanying Figures.

BRIEF DESCRIPTION OF THE DRAWING FIGURES

Figure 4B:
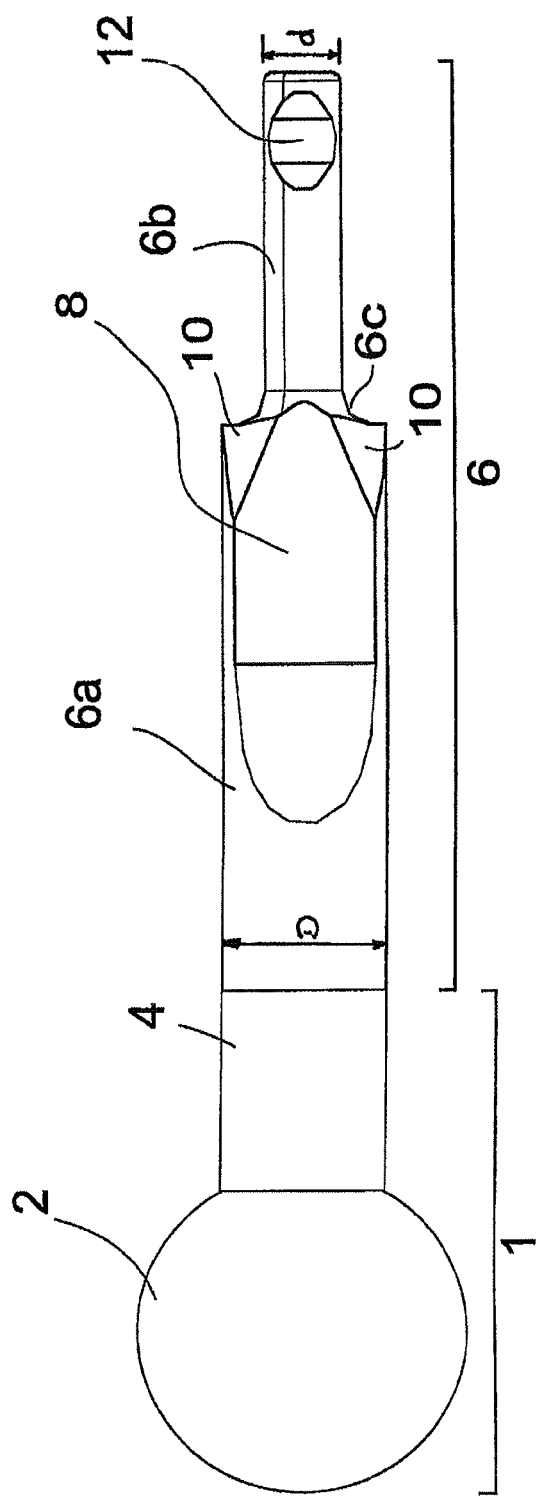
Figure 5:
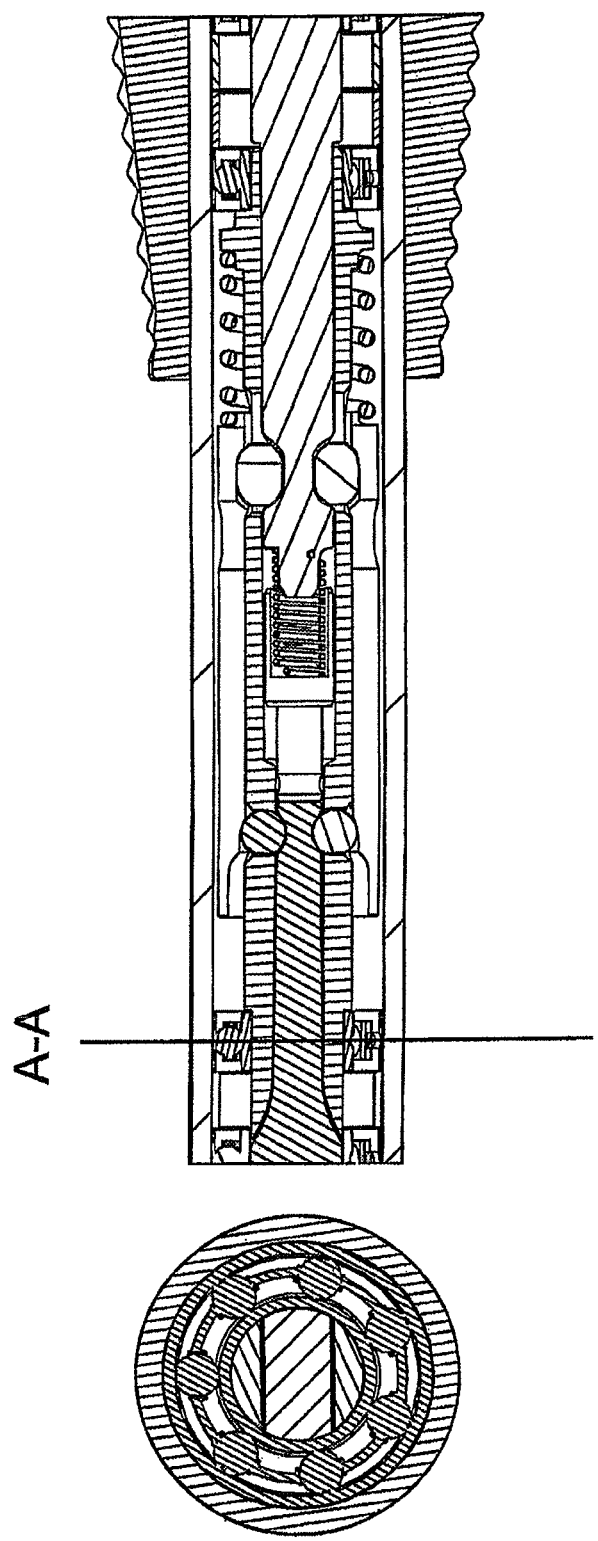
Figure 7A:
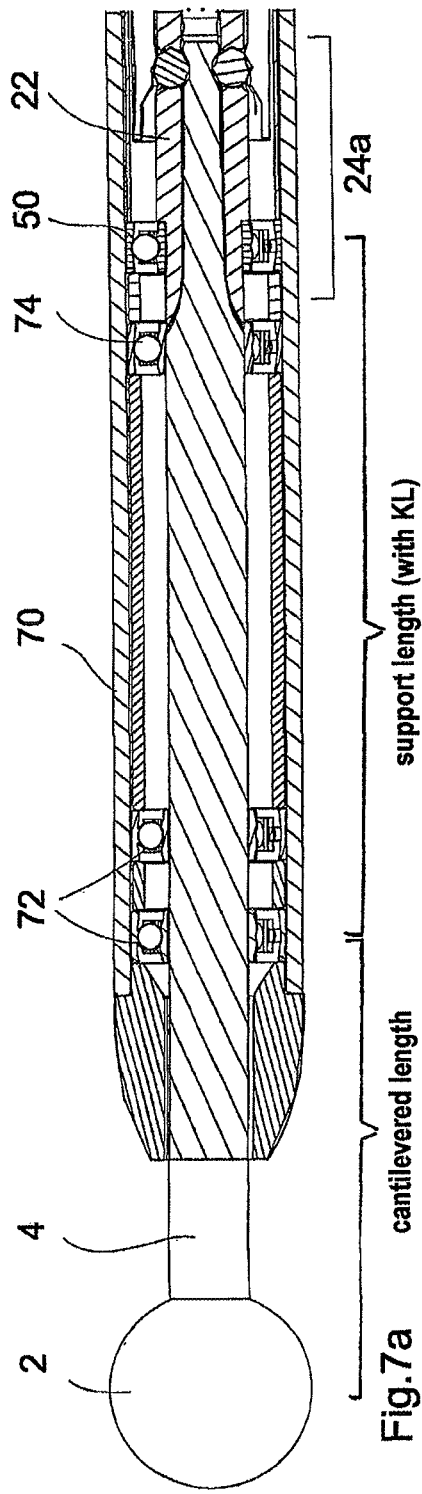
Figure 7B:
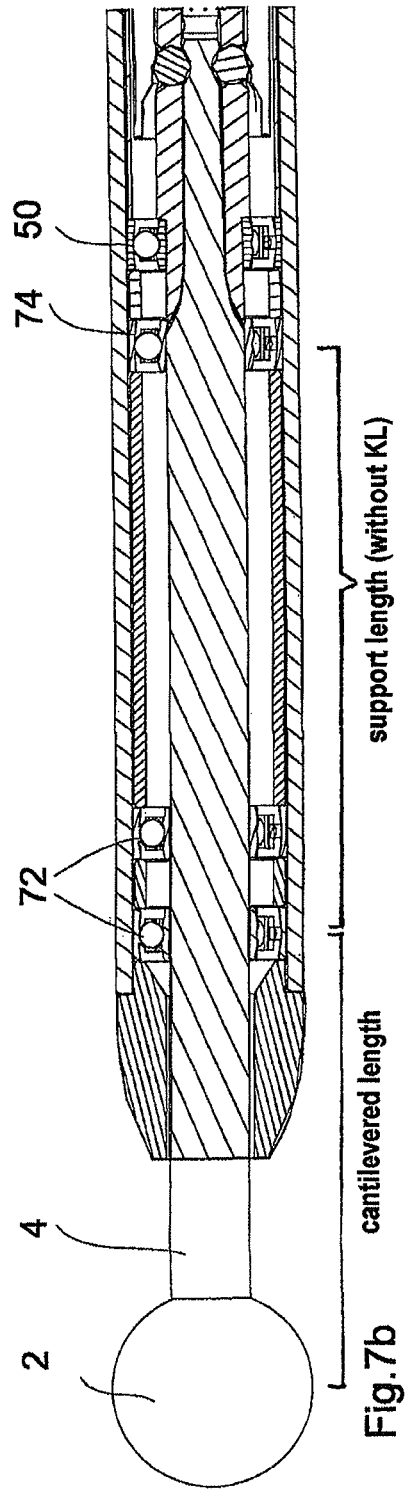
Figure 9:
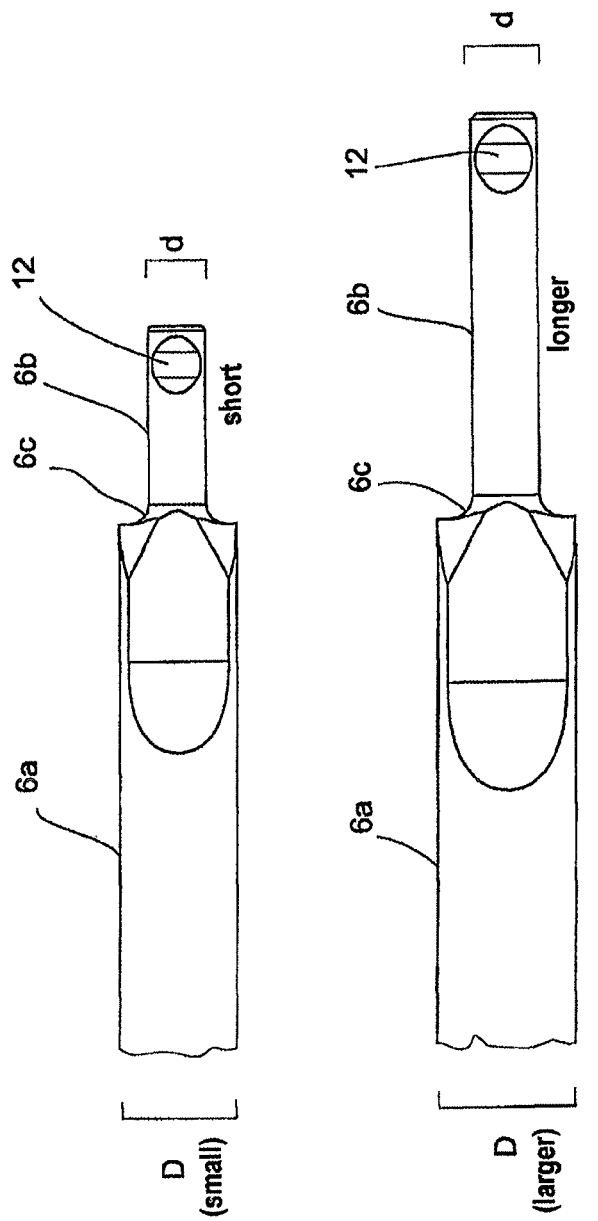
Figure 10:
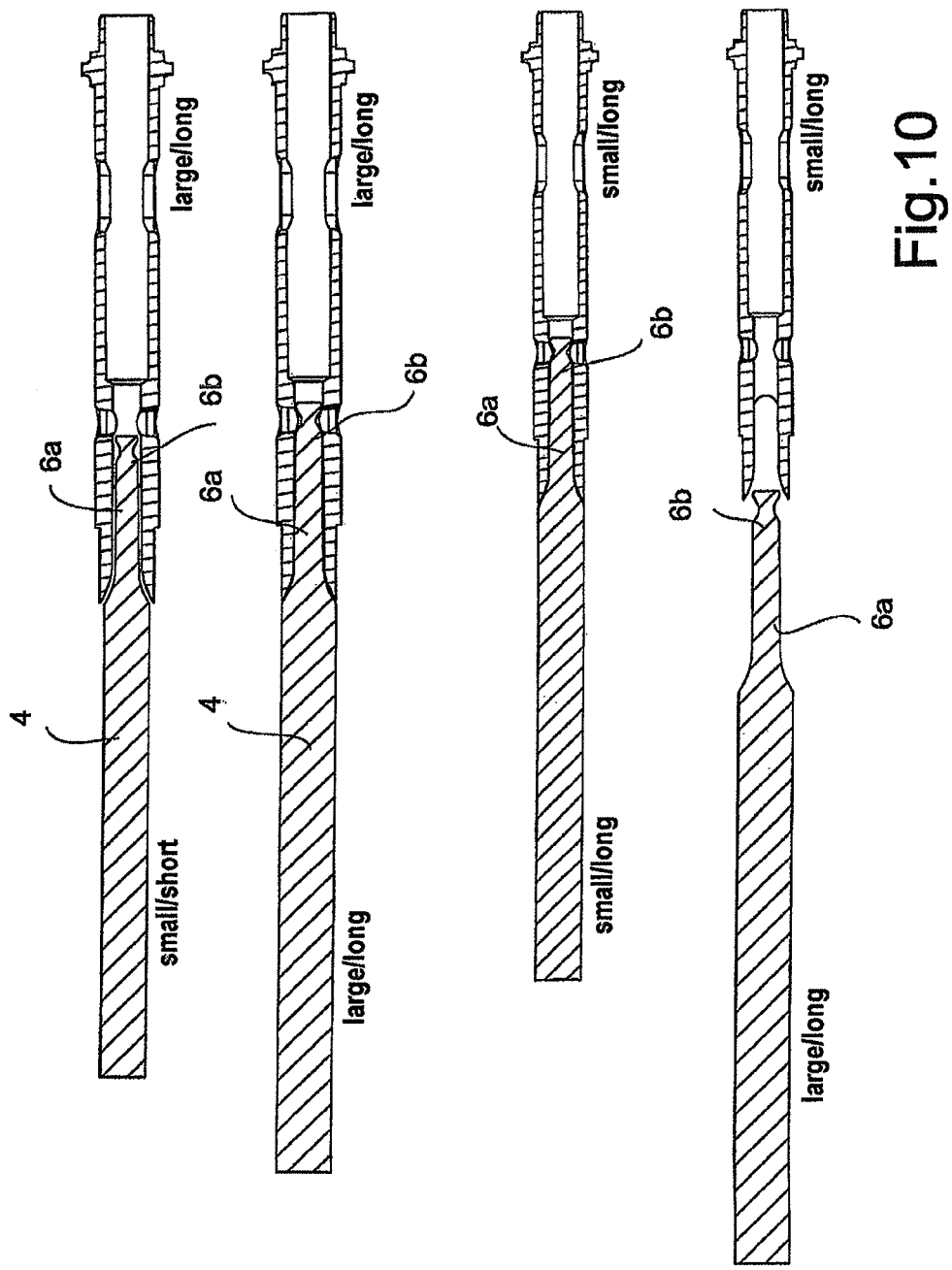
Figure 11:
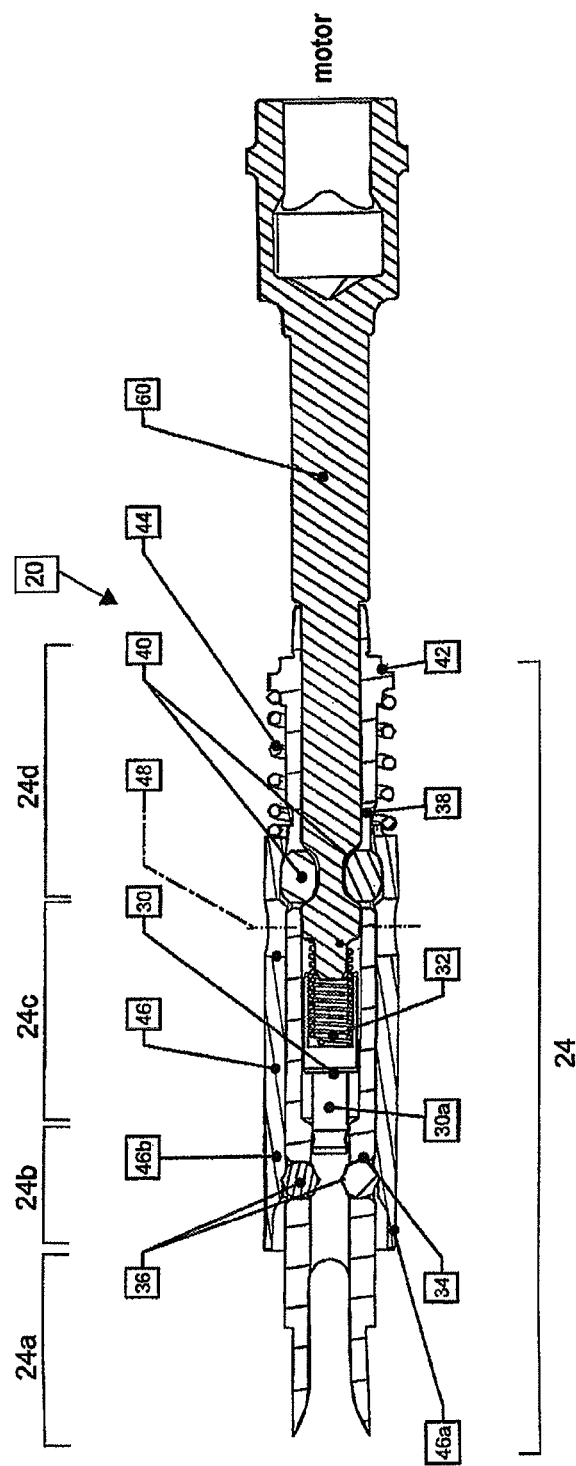
Figure 12:
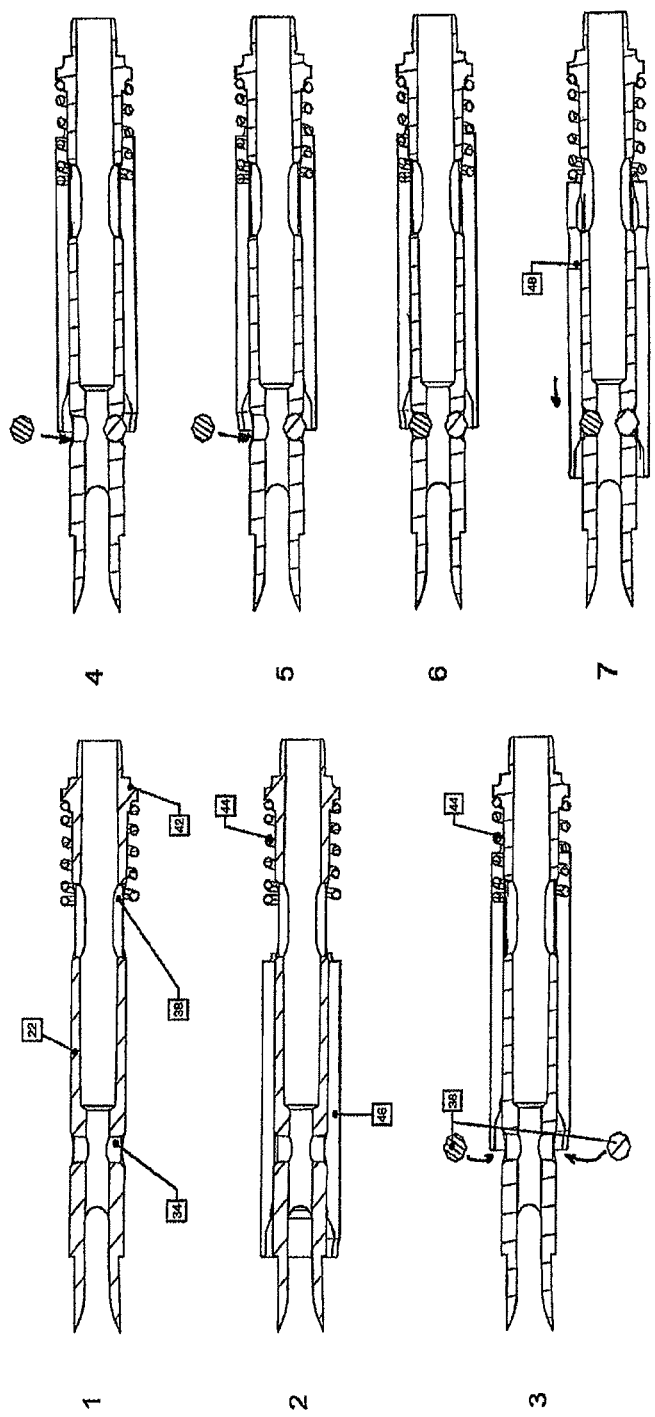
Figure 13:
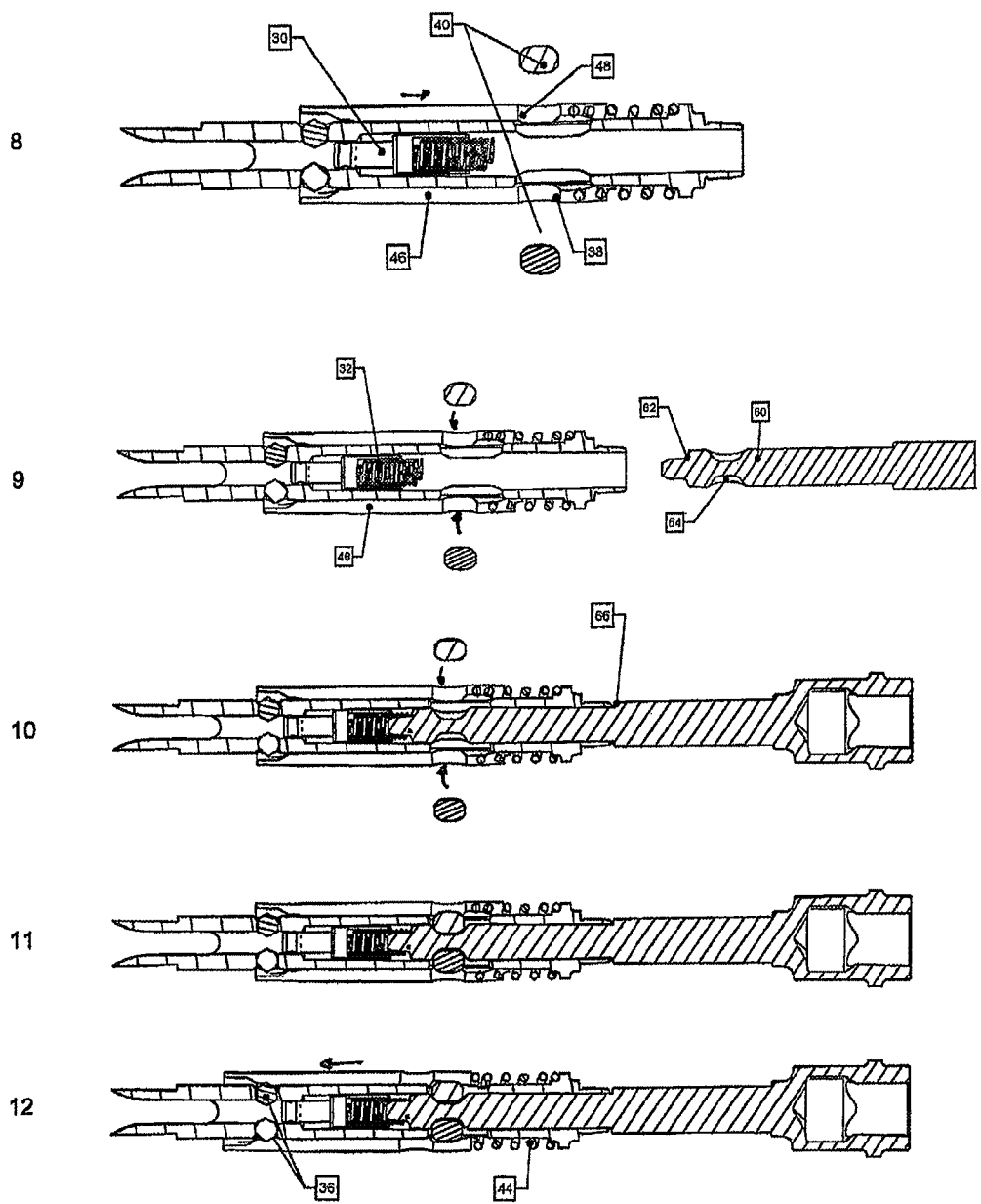
Figure 14:
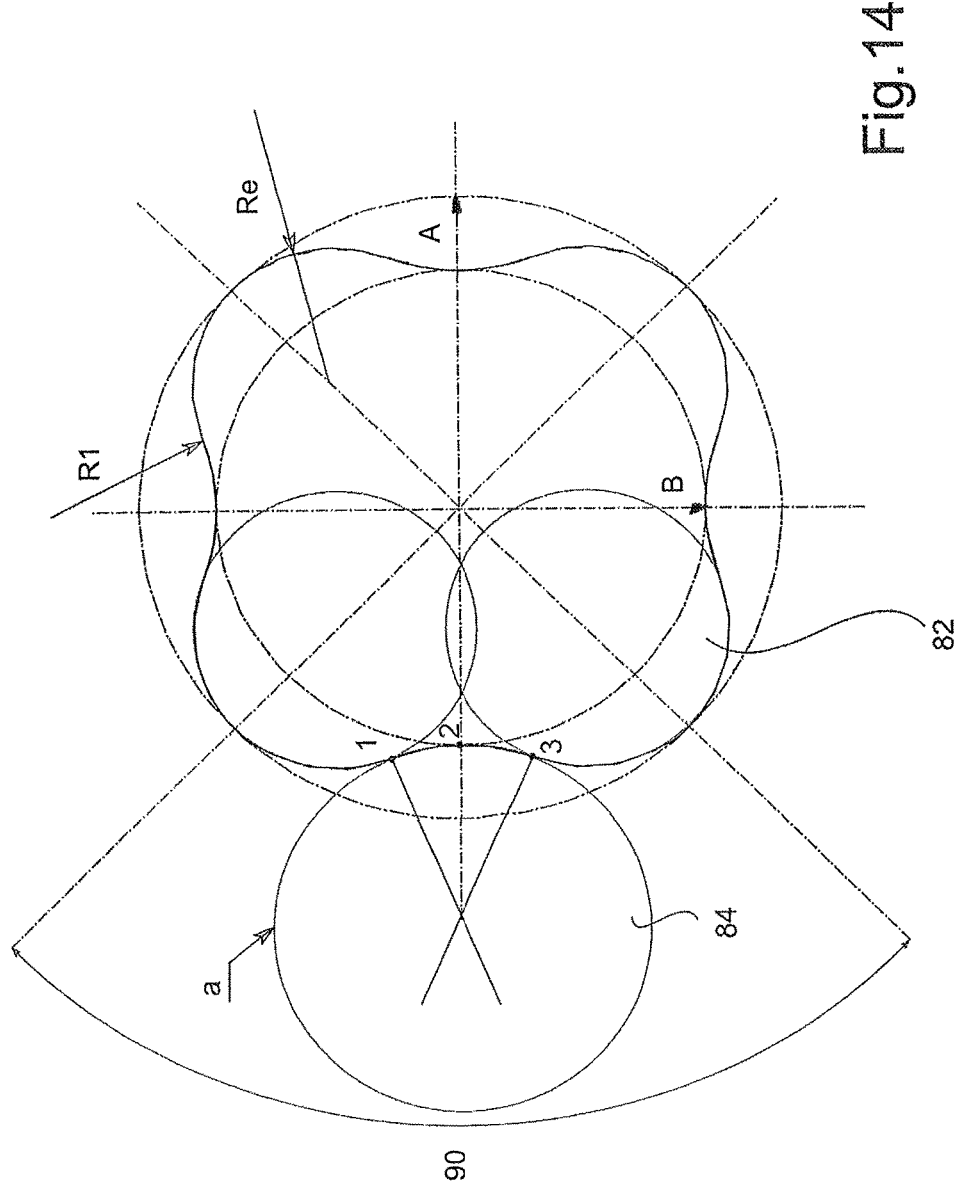
Figure 16:
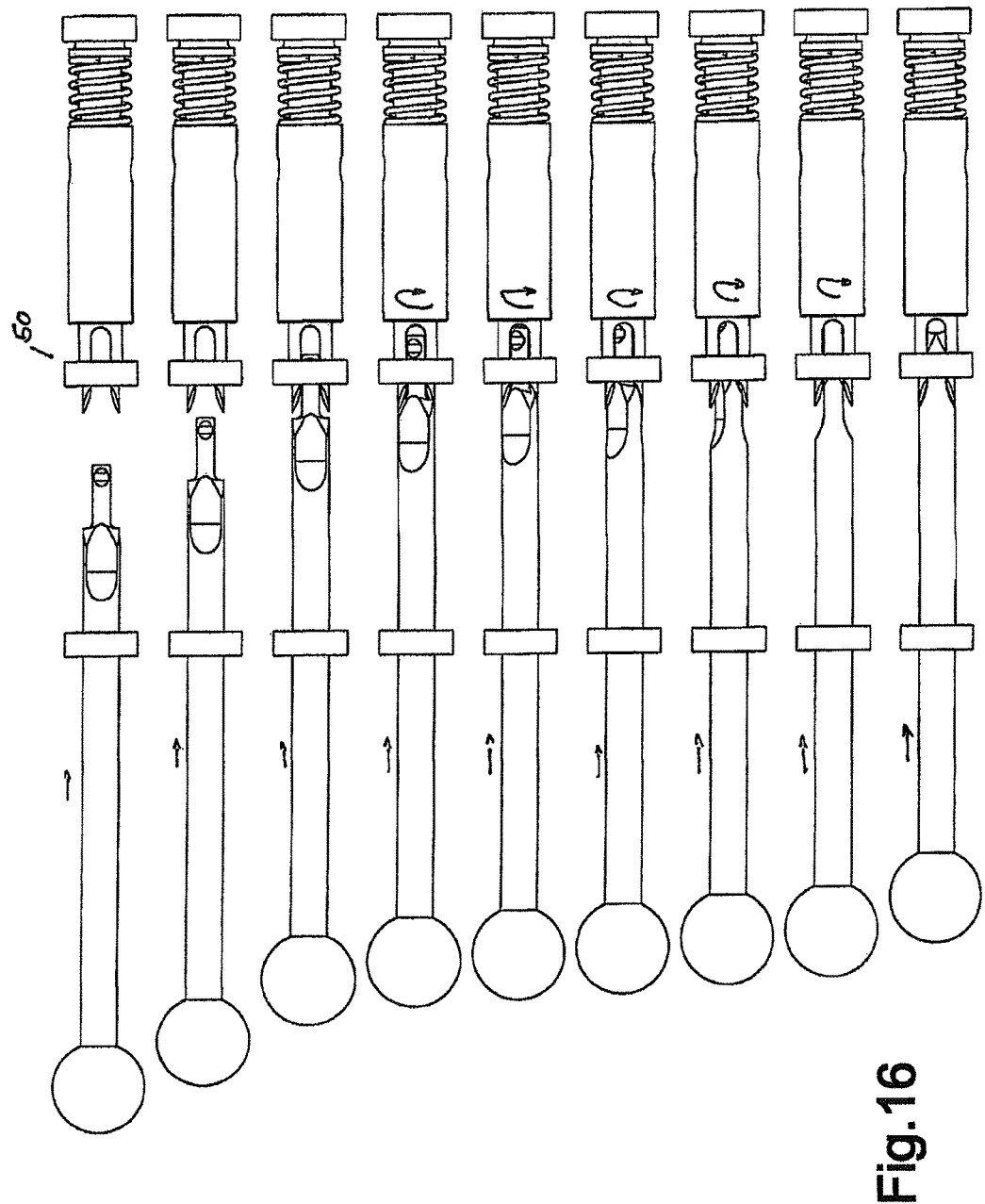

FIG. 1 shows the longitudinal section of a surgical instrument of the kind (including handpiece, handpiece shaft and tool) as it is also known from prior art and is to serve as a reference for a better illustration of the invention, FIG. 2 shows an enlarged view of the proximal shaft end portion of a tool for the surgical instrument according to FIG. 1, FIG. 3 shows the longitudinal section of a surgical instrument/system including handpiece, handpiece shaft and tool according to a preferred exemplary embodiment of the present invention, FIGS. 4a, 4b show an enlarged view of the proximal shaft end portion of a tool, according to the invention, for a surgical instrument according to FIG. 3, FIG. 5 shows an enlarged longitudinal section view of the instrument, according to the invention, in the area of the tool lock (of the tool mounting/tool lock), FIG. 6 shows an enlarged cross-sectional view of the tool mounting along the sectional line A-A according to FIG. 5, with the tool having been inserted already, FIGS. 7a and 7b each show a longitudinal section view of a first and second variant, according to the invention, of the bearing of the tool or the tool mounting in a comparison, FIG. 8 shows an enlarged view of the proximal tool shaft end portion according to a variant which represents an alternative to FIG. 4, FIG. 9 shows an example, according to the invention, of a coding possibility of different tool shafts for the foolproof use in different tool mountings (different handpiece shafts/handpieces according to the invention), FIG. 10 illustrates two examples of a correct and an incorrect selection of a tool for an instrument handpiece/handpiece shaft according to the invention (comprising a specific mounting) corresponding to the coding of the invention according to FIG. 9, FIG. 11 shows the longitudinal section of the surgical instrument handpiece of the invention (according to FIG. 1) in the area of the tool lock (tool mounting/tool coupling) without any tool, FIGS. 12 and 13 (chronologically) describe the assembly process for providing the tool lock (tool mounting) according to FIG. 12, FIG. 14 shows the cross-section of a cloverleaf The coupling according to the invention for a (detachable) (torque transmission) connection between the tool lock (tool mounting or torsion rod) and an output shaft within the surgical instrument handpiece for exchanging the distal handpiece shaft, FIG. 15 shows a male and a female part of the cloverleaf The coupling according to FIG. 14 and FIG. 16 shows the process of inserting a tool according to the invention into a tool mounting according to the invention step by step.

DETAILED DESCRIPTION

The surgical instrument or instrument system according to the invention consisting of an exchangeable (rotary) tool, a (universal) instrument handpiece and a possibly exchangeable handpiece shaft (including a torsion rod supported therein) basically includes four partial aspects according to the invention which can be claimed in the context of this invention independently or in combination with one another and are described in detail below. These partial aspects include:

the configuration of the proximal shaft end portion of the tool, according to the invention, of the present instrument system, the creation of a plug-in securing means in the form of a tool coding means for avoiding a fault in terms of selecting or using a tool, the construction of the tool lock according to the invention (or also of the tool mounting) within the handpiece shaft of the instrument handpiece as a part of the torque transmission train to the tool (for coupling the tool to the torsion rod within the handpiece shaft) as well as the tool lock construction in its operating portion and the development of a coupling/torque-proof connection between the tool lock (tool mounting) and the torsion rod within the handpiece shaft and an output shaft within the handpiece for facilitating the replacement of the distal handpiece shaft (including the tool lock supported therein and the torsion rod).

Tool According to the Invention Comprising Axially Separated Torque Transmission Means, Tool-Related Screw-in/Alignment Means and Axial Locking Means According to FIGS. 4a, 4b and 8, the tool 1 according to the invention substantially consists of a distal engagement segment or portion (facing the body) such as a drilling, milling, grinding or polishing head 2 to which a tool shaft 4 is attached preferably in the form of a substance-to-substance bond (or soldered, welded, pressed, etc.) which extends in proximal direction (facing away from the body). Said tool shaft 4 has a proximal end portion 6 for the torque-proof insertion of the tool 1 in a tool mounting (tool lock) of a surgical instrument handpiece or a handpiece shaft connected thereto as well as for an axial securing in the tool mounting.

To this end, the tool shaft 1 has its proximal end portion 6 subdivided in three functional areas which are axially spaced from one another (in succession) and are described in the following in chronological order starting from the distal end of the tool shaft end portion 6 (according to FIGS. 4a, 4b and 8 the left-hand end of the proximal end portion 6).

As can be taken from FIGS. 4a, 4b and 8, the entire tool shaft 4 according to the present invention first consists of a distal, essentially non-profiled shaft portion (directly adjoining the engagement segment 2), as well as an adjoining proximal shaft end portion 6 which for its part is serially subdivided in a distal portion 6a having a large shaft diameter and an external, profiled area as well as a proximal portion 6b having a small shaft diameter. The diameter ratio between the large and small shaft diameters D:d within the proximal shaft end portion 6 amounts to approximately 2:1. This means that the small shaft diameter d is substantially less than or equal to the half of the large shaft diameter D. More specifically, d<=0.6 D shall apply. Here, the large shaft diameter D is not formed so as to continuously taper toward the small shaft diameter d, but there is a radial shoulder 6c between the two shaft portions 6a, 6b of different diameters, optionally with a small inner radius for avoiding any notch effect.

In the area of the radial shoulder 6c, the large-diameter shaft portion 6a is formed according to FIG. 4a so as to have two diametrically opposing contact surfaces or planes 8 (a so-called dihedron), which approach each other in wedge-shaped manner toward the radial shoulder 6c and serve for introducing a torque into the tool shaft 4. These contact planes 8 may be formed in particular by grinding/milling or pressing/forging the initially unprofiled, round tool shaft 4. Additional glide surfaces or planes 10 (produced preferably in the same manner as the contact surfaces 8) are formed on the axial side edges of each contact surface 8 (in the region of the radial shoulder 6c), which are each aligned at an angle to the associated contact surface 8 and extend from an axial center region of each of the contact plane side edges toward the radial shoulder 6c in wedge-shaped fashion. This results in a shaft profile having six surfaces in the area of the radial shoulder 6c; said six surfaces consist of the two diametrically opposing contact planes 8 (dihedron) and, in the circumferential direction at both sides of each contact plane 8, respective glide or screw-in planes 10 breaking the corresponding side edge of the respective contact surface 8 in the area of the radial shoulder 6c and hence gradually reducing the width of the respective contact plane 8 toward the radial shoulder 6c.

According to FIGS. 4a and 4b, two notches or pockets 12 diametrically arranged on the circumference of the shaft are formed on (preferably milled into) the proximal end of the small-diameter shaft end portion 6b, whereby axially acting undercuts are formed on the shaft surface. As an alternative to these notches 12 and according to FIG. 8, it is also possible to produce a surrounding groove 12a on the proximal end of the small-diameter shaft end portion 6c by use of a lathe, whose groove depth essentially corresponds to the notch depth according to FIG. 4a, 4b. These notches 12 or the circumferential groove 12a serve(s) for axially locking the tool shaft 4 within a tool mounting as it will be described in the following.

The previously described shaft construction notably in the profiled tool shaft end portion 6 allows to achieve some advantages over the prior art according to FIGS. 1 and 2, which contribute to increase the maximum transferable torque from the torsion rod within the handpiece shaft to the tool 1:

Due to the basic separation of axial securing/locking section and torque entrainment section (with interposed screw-in aid) in two (possibly three) axially spaced shaft portions, these functional sections can be optimized independently of one another.

Here, the crucial point is that the functional section "locking" 6b is proximally arranged with respect to the functional section "torque entrainment" 6a. This allows to realize the locking portion 6b, which is not subjected to torsion/torque, with a small diameter as compared to the torque entrainment portion 6a and to form the radial shoulder 6c in this way.

The radial shoulder 6c in turn allows to form (to mill off), distally to the small-diameter locking portion 6b, two contact or torque transmission planes 8 with a larger axial length, in order to enlarge their respective surface area with respect to the prior art. Further, the radial shoulder 6c allows (as is illustrated in particular in FIG. 6) to remove in its region such a large amount of shaft material for forming the contact planes 8 that the remaining shaft diameter (in the region of the radial shoulder) between the two (wedge-shaped) planes 8 is nearly reduced to the half. This means that according to FIG. 6 the diameter Dm which can be utilized for torque transmission approaches the large shaft diameter D. If the dihedron formed in such a way is pushed into an axial gap of an entrainment shaft (which is described below), there is produced according to FIG. 6 a full circle with an optimal leverage ratio for torque transmission.

Up to now, the axial locking section according to FIGS. 1 and 2 has been arranged between the functional section "torque entrainment" and the tool engagement segment, limiting the maximum axial extent of the functional section "torque entrainment". Due to the resulting steeper wedge shape of the two contact planes, large axial forces act on the axial locking section. In addition, there is a weakening of the material of the locking portion arranged in the flow of torque. Now, provision is made to place the axial locking 6b proximal to the torque entrainment 6a (i.e. not between the torque entrainment and the engagement segment) outside the flow of torque. This allows to realize the wedge shape of the two contact planes 8 as a whole in a more flat design (with larger axial extension), reducing axial forces during torque transmission. Thus, the required (radial) installation space for the axial locking 6b can be made smaller (a small tool shaft diameter d is possible).

Finally, forming the radial shoulder 6c between the functional sections "torque transmission" 6a and "axial locking" 6b offers the possibility to arrange additional glide planes 10 as screw-in aid in the functional section "torque transmission" 6a. These glide planes 10 are each formed at both axial sides of the two contact planes 8 so as to be wedge-shaped, too, and break the side edges of the contact planes 8 in the area of the radial shoulder 6c, i.e. they are aligned at an angle relative to the respective contact plane 8. These glide planes 10 serve to orient the tool shaft 4 in the circumferential direction during inserting it in a tool mounting of the handpiece, to be more precise in such a manner that the two contact planes 8 are correctly guided into the tool mounting.

Tool According to the Invention Comprising a Tool Coding Means

As already explained above, an essential feature of the present invention is to arrange the functional section "axial locking" 6b proximal to the functional section "torque transmission" 6a. Furthermore, the tool shaft 4 according to the invention may also comprise all other features according to the previous description; these features, however, are only optional for the following inventive aspect "tool coding means".

Basically, a user wishes to minimize or eliminate malpractices in particular as a consequence of wrong surgical tools. This may be effected for instance by visual identifiers on the individual tools; in this case, however, the "human" factor cannot be eliminated as a source of error, which means that visual identifiers may be overlooked or misinterpreted/mixed up in reality, so that errors may occur during the selection of a specific tool which are detected only with its use and possibly too late. This source of error is the more important, the higher is the number of different tools which can be assigned to a universal handpiece in the context of an instrument/instrument system. In this case, it is thus advantageous and desirable if only a limited number of tools can be used for certain surgical intended purposes depending on a specific handpiece shaft (comprising an internally supported torsion rod) attached to the universal handpiece.

FIGS. 9 and 10 illustrate an advantageous variant of a tool coding means according to the invention, which allows to avoid the wrong selection of a tool.

The way of arranging the functional section "axial locking" 6b proximal to the functional section "torque transmission" 6a in such a manner that the former does not serve for transmitting any torque offers the basic (optional) possibilities to alter the axial length and/or the (small-diameter) shaft diameter d of said functional section 6b without having an (adverse) influence on the functional section "torque transmission" 6a. Thus, it is made possible to provide (or to combine) at least two (or more) different axial portion lengths (i.e. axial distance between radial shoulder 6c and radial pocket/circumferential groove 12/12a or the axially acting undercut) and/or at least two (or more) different (small-diameter) shaft diameters d, which are able to functionally cooperate only with correspondingly dimensioned tool mountings.

By way of example, FIG. 9 shows the two combinations "short locking portion" with "small shaft diameter" and "long locking portion" with "larger shaft diameter" with respect to the functional section "locking" 6b. Accordingly, the tool mounting (which will be described in detail below) according to FIG. 10 is basically formed such that the smaller shaft diameter indeed can be inserted in the mounting for the larger shaft diameter for torque transmission, but there will be no axial locking and therefore the tool 1 can again be retracted during checking the correct fit of the tool (upper picture). If the larger shaft diameter is inserted into said tool mounting, however, the axial locking will occur (second picture from above). In return, a mounting provided for the smaller shaft diameter does not allow to insert the larger shaft diameter at all (lower picture), whereas the smaller shaft diameter can be inserted and axially locked (second picture from below).

Here, reference is made to the fact that the length and the shaft diameter of the functional section "axial locking" 6b represent only two coding parameters which can be detected in a particular simple manner, but which can also be replaced or supplemented by other parameters. By way of example, the circumferential position of the pockets 12 with respect to the two contact planes 8 may serve for allowing a locking process only in the presence of the correct predetermined relative position (with a correspondingly correct orientation of the contact planes 8 relative to the tool mounting). The shape of the pockets 12 may also be altered, namely in such a manner that only compatible shapes on the part of the mounting result in a reliable axial locking. Finally, the portion "axial locking" 6b may be formed so as to comprise an additional shape (not illustrated) which cooperates according to the "key-keyhole-principle" with a corresponding shape in the tool mounting to allow the insertion of the tool shaft 4 (e.g. tongue-and-groove arrangement).

Handpiece Shaft Comprising the Tool Mounting (or Also Tool Lock) According to the Invention A tool mounting to be accommodated in a handpiece shaft, in particular for a (unitary) tool according to the previously described first and/or second aspect(s) of the invention has to meet several requirements substantially comprising the following:

Small radial dimensions to allow for their accommodation in a handpiece shaft which is narrow as is well-known.

A transfer of a sufficient working torque to the tool.

An ergonomically favorable and simple manual operation at least for releasing the tool inserted therein and preferably an automatic process of locking the tool (semi-automatic tool mounting).

Protecting the tool mounting and the tool in operation against self-acting dismantlement (such as in the presence of vibrations, shocks and/or impacts) for increasing the reliability of the instrument.

Simple and non-destructive assembly and disassembly of the mounting for cleaning or maintenance purposes, for instance.

The purpose of such a mounting within the handpiece shaft basically consists in displacing the tool mounting by any desired amount (and as far as possible) in distal direction, in this way limiting the tool shaft to an optimum (unitary) length with respect to the bending forces which are to be expected during use of the tool. This allows to provide such a (unitary) tool for different lengths and shapes of the shaft, with the shaft length between the handpiece and the tool mounting being spanned by a possibly bendable/flexible or rigid torsion rod supported in the handpiece shaft.

The known tool mounting schematically illustrated in FIG. 1 indeed has the potential regarding its spatial (in particular radial) dimensions to be installed within a handpiece shaft which is known per se and is of common design. However, in particular the cross pins for the connection of the accommodation tube with the torsion rod as well as for the torque-proof coupling of the accommodation tube with the torque transmission bolt supported therein and acting on the tool each represent a weak point in the torque transmission train, as has already been mentioned at the outset.

As shown in detail in FIG. 1, the inside torque transmission bolt is coupled at least to the outer accommodation tube by means of the one (thin) cross pin fitted in a transverse longitudinal hole formed therein. Such a (thin) cross pin is not able to reliably transfer a maximum torque which would be suitable for all purposes. In addition, the holes for the cross pin weaken the components which are to be connected and are very small anyway, i.e. the accommodation tube and the bolt. In addition and as already explained above, a further cross pin is provided for coupling the accommodation tube to the input or torsion rod, which causes the same problems. Notwithstanding the above, a process of connecting three components by means of the mentioned cross pins is very difficult and time-consuming in terms of manufacturing and assembly technology, especially with small dimensions as is the case with the generic handpiece shafts of the relevant known design. Thus, it is desirable to provide a tool mounting in particular for a tool having the structure described above, by means of which these problems are solved.

FIG. 11 shows a preferred exemplary embodiment of such a tool mounting 20 according to the invention, whose components are described below in detail as well as in terms of their cooperation with the tool 1 which is described at the outset.

First, the tool mounting or tool lock 20 of the invention and according to the preferred exemplary embodiment of the present invention comprises a radially inner tool accommodation tube (in the following referred to as an entrainment shaft) 22 comprising, at its distal end, a (beak-shaped) distal torque transmission portion and locking portion 24 slotted in the longitudinal direction; in its slotted torque transmission zone 24a (see also FIG. 6), said portion 24 has an outer diameter which is adapted to the large-diameter tool shaft portion 6a, and in its adjoining locking zone 24b it has an inner diameter adapted to the small-diameter tool shaft portion 6b. In this arrangement, the longitudinal slit 26 forms a slit width into which the tool shaft 1 can be inserted in the area of the two wedge-shaped contact planes 8 (see FIG. 6), so that the tool-side contact planes 8 rest against the beak-shaped axial protrusions 28 of the torque transmission zone 24a with extensive contact and together form a closed full-round profile (see FIG. 6).

The locking zone 24b is proximally adjoined by a cylindrical bolt mounting portion 24c which has a somewhat larger inner diameter than the locking zone 24b (the bolt 30 supported therein is referred to as a follower element below), with development of an inner radial shoulder which serves as an axial stop for the follower element 30 in distal direction. To this end, the follower element 30 has a distal portion 30a comprising an outer diameter corresponding to the small-diameter tool shaft portion "locking" 6b, which can thus be moved into the locking zone 24b of the entrainment shaft 22, as well as a proximal portion with a larger outer diameter 30b, where the follower element 30 is guided in the entrainment shaft 22 in sliding manner. Formed between the two portions 30a, 30b of the follower element 30 is an outer ring shoulder which cooperates with the inner ring shoulder of the entrainment shaft 22 in distal direction.

Finally, a follower spring 32 for the follower element 30 is provided in the mounting portion 24c; said follower spring biases the follower element 30 in distal direction and in this way urges it against the inner ring shoulder in the entrainment shaft 22. In this position, the small-diameter distal portion 30a of the follower element 30 is completely retracted in the locking zone 24b of the entrainment shaft 22.

It should be mentioned here that the locking zone 24b of the entrainment shaft 22 is provided with a number (at least one) of radial through-holes 34 which are uniformly spaced along the circumference and serve for receiving locking balls 36 for the inserted tool 1, as will be described below.

In the proximal prolongation of the mounting portion 24c for the follower element 30, the entrainment shaft 22 forms a coupling/plug-in portion 24d for a drive/torsion rod 60, the latter being rotatably supported in a handpiece shaft (not illustrated in FIG. 11, but see FIG. 3, for example) of a (universal) handpiece.

In the area of this plug-in portion 24d, also the entrainment shaft 22 comprises a number (at least one) of radial openings or apertures 38 which are uniformly spaced along the circumference and lie on a circular plane; said apertures have an approximately oval cross-section extending in axial direction of the entrainment shaft 22 in each case. These radial openings 38 serve for receiving preferably oval rolling bodies 40 (referred to as entraining elements in the following) via which the entrainment shaft 22 is coupled to the inserted torsion rod 60 in axially fixed and torque-proof manner, which will be described in more detail below. It should be noted here that balls may also be used instead of oval (cylindrical) rolling bodies with rounded end faces.

At the proximal end of the plug-in portion 24d, the entrainment shaft 22 further comprises a circumferential radial protrusion 42 which serves as a spring seat of an outer closure spring 44.

A closure sleeve 46 is supported around the entrainment shaft 22 so as to be rotatable and axially shiftable. Said sleeve has a distal ball releasing zone 46a with a large inner radius and a proximally adjoining ball retaining zone 46b with a small inner radius, which is also guided on the outside of the entrainment shaft 22 in sliding manner.

Formed in a proximal end portion of the closure sleeve 46 is a number (preferably two) of radial through-holes 48 with a longitudinally oval (or round) cross-section, which serve for filling the apertures 38 provided in the entrainment shaft 22 with the oval/barrel-shaped, rounded rolling bodies 40. Each of said oval (larger length than width) through-holes 48 of the closure sleeve 46 is prolonged to form a mounting pocket on the inner circumference of the closure sleeve 46, so that the closure sleeve 46 can axially move over the already inserted rolling bodies/entraining elements 40 and prevent them from falling out. At the same time, the mounting pockets have such a shape that the closure sleeve 46 can be rotated by a defined angle with respect to the entrainment shaft 22, so that according to the following description the rolling bodies 40 and also the locking balls 36 cannot fall out any more even if the closure sleeve 46 is moved back to an axial releasing position.

Finally, the closure spring 44 is arranged axially between the closure sleeve 46 and the outer radial protrusion 42 of the entrainment shaft 22, and urges the closure sleeve 46 in distal direction into an axial locking position.

The assembly and the mode of operation of the tool mounting 20 according to the invention is explained in more detail below on the basis of FIGS. 11 to 13 in connection with FIG. 5.

According to FIGS. 12 and 13, fitting the tool mounting 20 to a torsion rod 60 begins with slipping the outer closure spring 44 over the entrainment shaft 22; subsequently, the closure sleeve 46 is put on the entrainment shaft 22 from distal direction, so that the outer closure spring 44 comes to lie between the closure sleeve 46 and the outer radial protrusion 42 on the entrainment shaft 22 (see illustrations 1 and 2 of FIG. 12).

As a next step, the closure sleeve 46 is pushed against the outer closure spring 44 into its axial filling or releasing position, whereby the through-holes 34 in the locking zone 24b of the entrainment shaft 22 are exposed. At that moment, the locking balls 36 can be placed in said through-holes 34 through an assembly groove provided inside the closure sleeve 46, said locking balls projecting radially inwards (see illustrations 3 to 6 of FIG. 12). Subsequently, the closure sleeve 46 can be released whereby it is axially moved to the ball locking position by means of the outer closure spring 44, in which position the closure sleeve 46 is shifted over the locking balls 36 and hence prevents them from falling out radially. The locking balls 36 simultaneously serve as an axial stop for the closure sleeve 46, which has its distal inner circumference provided to this end with a small inner radial shoulder axially resting against the locking balls 36 in the retaining or locking position of the closure sleeve 46 (see illustration 7 of FIG. 12). With this, the preliminary assembly of the tool mounting 20 according to the invention is completed.

FIG. 13 illustrates the process of fitting the tool mounting 20 to a torsion rod 60.

First, the follower element 30 and then the inner follower spring 32 is inserted into the entrainment shaft 22 from proximal direction, the distal portion 30a of the follower element 30 axially resting against the locking balls 36. Subsequently, the torsion rod 60 is put into the entrainment shaft 22 from proximal direction. The torsion rod 60 has its distal end formed like a radial shoulder 62 as a spring seat for the already inserted inner follower spring 32. Further, the torsion rod 60 comprises at its distal end portion a number of outer pockets 64 which are uniformly spaced along the circumference and serve for receiving the entraining elements (oval rolling bodies) 40. Finally, the circumferential side of the torsion rod 60 optionally forms a shaft step 66 working as an axial stop for the entrainment shaft 22.

As soon as the entrainment shaft 22 rests against the optional axial stop 66 of the torsion rod 60, the radial outer pockets 64 of the torsion rod 60 exactly overlap the proximal apertures 38 of the entrainment shaft 22 as well as the fill openings 48 of the closure sleeve 46 pushed into the axial fill/releasing position (see illustrations 8 to 10 of FIG. 13). This is the time to insert the oval entraining elements 40 via the fill openings 48 of the closure sleeve 46 into the apertures 38 of the entrainment shaft 22 as well as into the outer pockets 64 of the torsion rod 60 (see illustration 11 of FIG. 13). As a final step, the closure sleeve 46 is released which is automatically moved axially to the locking position in distal direction by the closure spring 44; in said locking position, the closure sleeve 46 has moved over the locking balls 36 and the entraining elements 40 and hence prevents them from falling out radially. As a last step, the closure sleeve 46 is rotated by a defined angle with respect to the entrainment shaft 22. This allows to prevent the balls 36 and preferably also the entraining elements 40 from unintentionally falling out through the fill openings 48 of the closure sleeve 46 even if the closure sleeve 46 is again retracted into the ball releasing position during normal operation. This means that the axial position of the closure sleeve 46 for filling it with the entraining elements 40 as well as radially releasing the balls 36 during insertion of a tool 1 is preferably the same. The angular position of the closure sleeve 46 with respect to the entrainment shaft 22 in the filling position, however, is different from the angular position in the releasing position.

With this, the process of fitting the tool mounting 20 to the torsion rod 60 is completed.

As is made plain by the above description of the assembly process, radially outer entraining elements 40 preferably in the form of oval rolling bodies are provided for a torque transmission from the torsion rod 60 to the entrainment shaft 22. Thus, these elements have a large effective force application surface and thus are capable of transferring substantial torques without getting sheared off. At the same time, the entraining elements serve for axially securing the tool mounting on the torsion rod. Owing to the radially outer positioning, a maximal leverage for torque transmission is achieved, too.

According to the invention, the torque is transferred to the tool shaft 4 not via the follower element (bolt) 30 as is the case with the mentioned prior art, but directly via the entrainment shaft 22. This reduces the number of the components incorporated in the torque transmission train, which simplifies the assembly as a whole.

The mode of operation of the tool mounting 20 according to the invention is explained in more detail below on the basis of FIGS. 5, 7a, 7b and 16.

First, it should be noted that the tool mounting 20 has to be rotatably supported within a handpiece shaft which can be coupled to a universal handpiece. To this end, a radial bearing (KL) 50 such as a ball, roller or needle bearing comprising an inner and outer race is preferably provided and fitted to the entrainment shaft 22 in the torque transmission zone 24 provided with the longitudinal slit; thus, it counteracts a spreading apart of the beak-shaped axial protrusions 28 if a torque is transmitted to the contact planes 8 of the tool shaft 4. In addition, the support/cantilevered ratio being present on the tool shaft 4 is improved by such a ball bearing (KL) 50 in the longitudinally slotted torque transmission zone 24a, as is shown in particular in FIGS. 7a and 7b.

FIG. 7a shows the installation situation of a tool 1 in a tool mounting 20 according to the invention comprising a radial bearing (KL) 50 in the torque transmission zone 24a of the entrainment shaft 22. As can be taken from this Figure, the tool shaft 4 extending distally out of the handpiece shaft 70 is supported by at least one distal bearing (preferably two distal bearings) 72 and at least one proximal bearing 50, 74, in order to absorb tool contact forces and cutting forces which act on the tool shaft 4 as bending forces. Accordingly, if the at least one proximal radial bearing 50 is positioned in the torque transmission zone 24a of the tool mounting 22, there is a support length between the distal and proximal bearing 72, 50 which is significantly larger than the cantilevered length between the distal bearing 72 and the tool engagement segment 2.

On the contrary, FIG. 7b shows a reference example in which the bearing 74 provided distal to the torque transmission zone 24a is assumed as the proximally last radial bearing (actually no additional ball bearing (KL) 50). In this case, the support length is shortened as compared to the cantilevered length. It is obvious that the load on the radial bearings 72, 74 is enlarged in the latter case according to FIG. 7b and hence show higher wear. The maximum admissible load is small as well.

The procedure of inserting the tool 1 according to the invention into the tool mounting 20 according to the invention is illustrated in detail in FIG. 16.

First, the tool shaft 4 is approached to the torque transmission zone 24a of the tool mounting 20, possibly even in an incorrect relative rotational position; in this case, the tool-side glide surfaces 10 make contact first with the two beak-shaped axial protrusions 28 of the tool mounting 20. Due to their orientation, the entrainment shaft 22 is rotated automatically until the two contact planes 8 face the radially outer axial protrusions 28. Now, the tool shaft 4 can be farther inserted into the tool mounting 20, the tool-side contact surfaces or planes 8 being guided in sliding manner between the beak-shaped axial protrusions 8. The radial bearing 50 which is also shown in FIG. 16 prevents the beak-shaped or forked axial protrusions/lugs 28 from being spread apart.

For inserting the tool shaft 4, the closure sleeve 46 first is in its retracted releasing position in which the locking balls 36 can be pushed radially outward. This is effected by the follower element 30 (bolt) whose distal portion 30a is pushed radially between the locking balls 36 by the follower spring 32, keeping said balls in radially outward position. The balls 36 which are pushed radially outwards will then keep the closure sleeve 46 axially in its releasing position.

During the penetration of the tool shaft 4 into the tool mounting 20, however, the end face of the tool shaft-side locking portion 6b hits the follower element 30 and displaces it in axial direction against the pretensioning force of the follower spring 32 until the pockets/circumferential groove 12/12a are/is situated in the locking portion 6b of the tool shaft 4 in the area of the locking balls 36. In this moment, the balls 36 are pushed inwards and thus come to lie in the circumferential groove 12a or the pockets 12 of the tool shaft 4 which is effected by the closure sleeve 46 due to the axially acting spring preload and a corresponding conical shape on the inner circumferential side of the closure sleeve 46 (not shown in further detail). At the same time, the closure sleeve 46 due to the spring preload is moved further in distal direction to its locking position. With this, the tool 1 is axially secured, and a torque can be transmitted from the torsion rod 60 via the entraining elements 40 and the entrainment shaft 22 to the contact planes 8 of the tool shaft 4.

In order to remove the tool 1, the closure sleeve 46 is (manually) retracted against the closure spring 44 into the releasing position in proximal direction to release the locking balls 36 radially. If the tool shaft 4 is then pulled out of the mounting 20, the follower element 30 follows the tool shaft 4 automatically due to the follower spring 32 and in this way comes to lie radially between the locking balls 36 in order to keep them pushed radially outward. This is why the tool mounting 20 remains in this releasing position to axially lock a newly inserted tool shaft 4 in automated fashion. Thus, the present tool mounting 20 according to the invention may also be referred to as a semi-automatic tool mounting (automatic locking and manual release).

Coupling Between the Tool Mounting or Torsion Rod and a Handpiece-Sided Gearing Mechanism Train As already explained at the outset, one aspect of the present invention is the possibility to use always the same tool for different handpiece shafts. The handpiece shafts have such a construction that they can be coupled to a single, universal handpiece in which the tool drive and/or the torque transmission train/gearing mechanism is/are housed. This means that a torsion rod has to be pre-installed within the respective handpiece shaft; the distal end of said torsion rod has to be provided with the tool mounting preferably according to the above description and its proximal end has to be provided with a coupling which in the course of firmly coupling the handpiece shaft to the handpiece (preferably to its housing) simultaneously comes into operative engagement with the torque transmission train to allow a torque transmission to the torsion rod.

In the first place, a coupling of this type has to transfer torques, but must also permit an axial displacement of the drive shaft so that the tool mounting can be unlocked and dismounted, for example. Moreover, the coupling should possess sufficient guiding qualities in order to be able to save—at least in this area—further radial bearings (ball bearings) for supporting the coupling.

Up to now, the coupling in question between the torsion rod (within the exchangeable handpiece shaft) and the torque train (within the handpiece) has been realized by a so-called dihedron which is comparable to the previously described torque transmission portion, according to the invention, between the tool shaft and the tool mounting. However, such a coupling (without surrounding radial bearing) has the basic problem of an insufficient torsional rigidity in the given (narrow) constructional space, which might result in an early failure of the cooperating coupling components. In addition, said construction achieves only insufficient guiding qualities.

An alternative to the mentioned dihedron is the commonly known cross-type solution. In this case, the male coupling piece is provided on the side of the torsion rod with webs crossing at an axially central position and capable of being inserted into a correspondingly shaped female coupling piece, whereby the surface area, available for torque transmission, on the side faces of each web can be enlarged as a whole. This solution, however, also afflicted with problems insofar as there is no optimum distribution of the torsional rigidity between the male and the female coupling piece, so that maximum transferrable torque is limited here, too.

In order to solve this problem, a cross-sectional geometry for the coupling pieces (male and female) is required which makes optimum use of the given constructional space in the case of a surgical handpiece of the relevant kind with respect to the torsion-related moment of area, at the same time allows an axial displacement of the two coupling components relative to each other and does not come into a self-locking condition due to the special shape.

In the course of developing the coupling according to the invention, it has turned out that the form fit for torque transmission is the less, the more the entrainment contour resembles a circle. Further, the lower the number of corners of the entrainment contour, the more form-locking is the coupling combination (with decreasing section modulus). As a whole, a cloverleaf coupling 80 comprising four lobes turns out to be a particularly advantageous cross-sectional shape of the coupling for a surgical instrument of said kind. FIG. 14 illustrates an optimized cross-section of a four-lobed cloverleaf shape according to a preferred exemplary embodiment of the invention.

Accordingly, the cross-sectional shape, according to the invention, of the coupling 80 is based on four equal circles 82 with a small radius Re, which define the four corners of the coupling shape and are arranged so as to be angularly offset by 90° relative to each other. The distance of the respectively neighboring centers of the circles which are within the coupling shape is slightly smaller as the unitary circle diameter Re, so that the respectively neighboring circles 82 intersect.

On a center axis between two neighboring intersecting circles 82 and outside the coupling shape, a further center of circle is set where a circle 84 with a larger radius Ri is drawn around it in each case. The respective position of said outer, further center of circle as well as the larger radius Ri are set such that the contour of the outer circle 84 continuously merges with the contour of the two corner-side inner circles 82 and hence connects all neighboring corner circles 82 to each other by forming a cavity. This means that the outer circle 84 is tangential to the two inner corner circles 82 in the contact points, creating a continuous cross-sectional contour (without corners and edges) with four marked convex corner circles 82 and four smoothly concave side circles 84.

In geometrical terms, the cross-sectional contour can be defined according to the preferred exemplary embodiment as follows:

According to FIG. 14, the value A designates the diameter of a circumferential circle with a centric center of circle and radially outer contact points on all corner circles. The value B represents the clear measure between two opposing side circles, i.e. the diagonal distance of those points on two opposing side circles which represent the innermost points on the cross-section.

Accordingly, these values A, B are in a proportion relative to each other according to formula (1):

$$B = kB * A \qquad (1)$$

with $0.6 < kB < 0.9$.

The radius Re of each corner circle is in a proportion to the value A according to formula (2):

$$Re = kRe * A \qquad (2)$$

with $0.6 < kRe < 0.9$.

The radius Ri of each side circle is in a proportion to the value A according to formula (3):

$$Ri = kRi * A \qquad (3)$$

with $0.8 < kRi < 1.5$.

FIG. 15 shows that the male as well as the female coupling piece has a corresponding cross-sectional shape, with a specific oversize of the female coupling piece.

The invention claimed is:

1. A coupling for connecting a torsion rod supported in a tool shaft or a tool to a torque transmission train or drive, the coupling comprising two axially pluggable male and female coupling pieces and accommodated in a surgical handpiece, the coupling pieces each comprising a cross-sectional shape, wherein the cross-sectional shape corresponds to a four-leaved cloverleaf having a pitch-circle cross-section,
   wherein the cross-sectional shape comprises four corner circles defining four equal corner circle lines, each corner circle line having a radius and a center, the corner circle lines defining four corners of the cross-sectional shape,
   wherein adjacent corner circle lines are connected to each other by a side circle line having a radius larger than the radius of each corner circle line, said side circle line having a center situated outside the cross-sectional shape, and
   wherein a distance between the centers of adjacent corner circle lines is smaller than the diameter of each corner circle so that adjacent corner circles intersect.

2. The coupling according to claim 1, wherein each side circle line has a concave cross-sectional contour which merges into convex contours of two of the corner circle lines, thus forming the cross-sectional shape that corresponds to the four-leaved cloverleaf.

3. The coupling according to claim 2, wherein each of the side circle lines adjoins two adjacent corner circle lines in a tangential manner, so that an overall contour of the coupling results in a continuous circumferential line.

4. The coupling according to claim 1, wherein the cross-sectional shape meets a formula:

$$B = kB * A, \qquad (1)$$

with $0.6 < kB < 0.9$,
   wherein A is the diameter of a circumscribed circle which has a center in a center of the cross-sectional shape and has radially outer contact points on all corner circles, and wherein B is a distance between two of the side circle lines that are opposed to one another.

5. The coupling according to claim 4, wherein the cross-sectional shape further meets:

$$Re = kRe * A, \qquad (2)$$

with $0.6 < kRe < 0.9$, and Re=same radius of each corner circle line, and $$Ri = kRi * A, \qquad (3)$$

with $0.8 < kRi < 1.5$, and Ri=same radius of each side circle line.

6. The coupling according to claim 1, wherein, of the two axially pluggable male and female coupling pieces, a longitudinal axis of the male coupling piece is coaxial to a longitudinal axis of the female coupling piece.

* * * * *